United States Patent [19]
Wölfel et al.

[11] Patent Number: 5,530,096
[45] Date of Patent: *Jun. 25, 1996

[54] ISOLATED, TYROSINASE DERIVED PEPTIDES AND USES THEREOF

[75] Inventors: Thomas Wölfel, Mainz, Germany; Aline Van Pel, Brussels, Belgium; Vincent Brichard, Brussels, Belgium; Thierry Boon-Falleur, Brussels, Belgium; Etienne DePlaen, Brussels, Belgium; Pierre Coulie, Brussels, Belgium; Jean-Christophe Renauld, Brussels, Belgium; Bernard Lethe, Brussels, Belgium

[73] Assignee: Ludwig Institute For Cancer Research, New York, N.Y.

[*] Notice: The term of this patent shall not extend beyond the expiration date of Pat. No. 5,487,974.

[21] Appl. No.: 203,054

[22] Filed: Feb. 28, 1994

Related U.S. Application Data

[63] Continuation-in-part of Ser. No. 81,673, Jun. 23, 1993, Pat. No. 5,487,974, which is a continuation-in-part of Ser. No. 54,714, Apr. 28, 1993, which is a continuation-in-part of Ser. No. 994,928, Dec. 22, 1992, abandoned.

[51] Int. Cl.$^6$ .............................. C07K 7/06; A61K 38/08
[52] U.S. Cl. ............................................................. 530/328
[58] Field of Search ......................... 514/15, 16; 530/328

[56] References Cited

U.S. PATENT DOCUMENTS 4,898,814  2/1990  Kwon ........................................ 435/6

OTHER PUBLICATIONS

Roitt et al., *Immunology*, Moshy–Yearbook, St. Louis, Mo., pp. 6.10–6.11, 1993.

Brichard, et al, "The Tyrosinase Gene Codes for an Antigen Recognized by Autologous Cytolytic T Lymphocytes on HLA–A2 Melanomas", J. Exp. Med. 178: 489–495 (1993).

Coullie, et al, "Genes Coding For Tumor Antigens Recognized by Human Cytolytic T. Lymphocytes", J. Immunotheray 14: 104–109 (1993).

Slingluff, et al, "Recognition of Human Melanoma Cells by HLA–A2.1 Restricted Cytotoxic T Lymphocytes As Mediated By At Least Six Shared Peptide Epitopes", J. Immunol. 150(7): 2955–2963 (Apr. 1, 1993).

Barinaga, "Getting Some 'Backbone': How MHC Binds Peptides" Science 257: 880–881 (Aug. 14, 1992).

Falk, et al, "Allele Specific Motifs revealed by sequencing of self–peptides eluted from MHC molecules", Nature 351: 290–296 (May 23, 1991).

Wolfel, et al, "Lysis of Human Melanoma Cells by Autologous Cytolytic T Cells Clones", J. Exp. Med. 170: 797–810 (Sep. 1989).

*Primary Examiner*—Robert D. Budens
*Attorney, Agent, or Firm*—Felfe & Lynch

[57] ABSTRACT

The invention relates to the identification of complexes of human leukocyte antigen molecules and tyrosinase derived peptides on the surfaces of abnormal cells. The therapeutic and diagnostic ramifications of this observation are the subject of the invention.

1 Claim, 11 Drawing Sheets

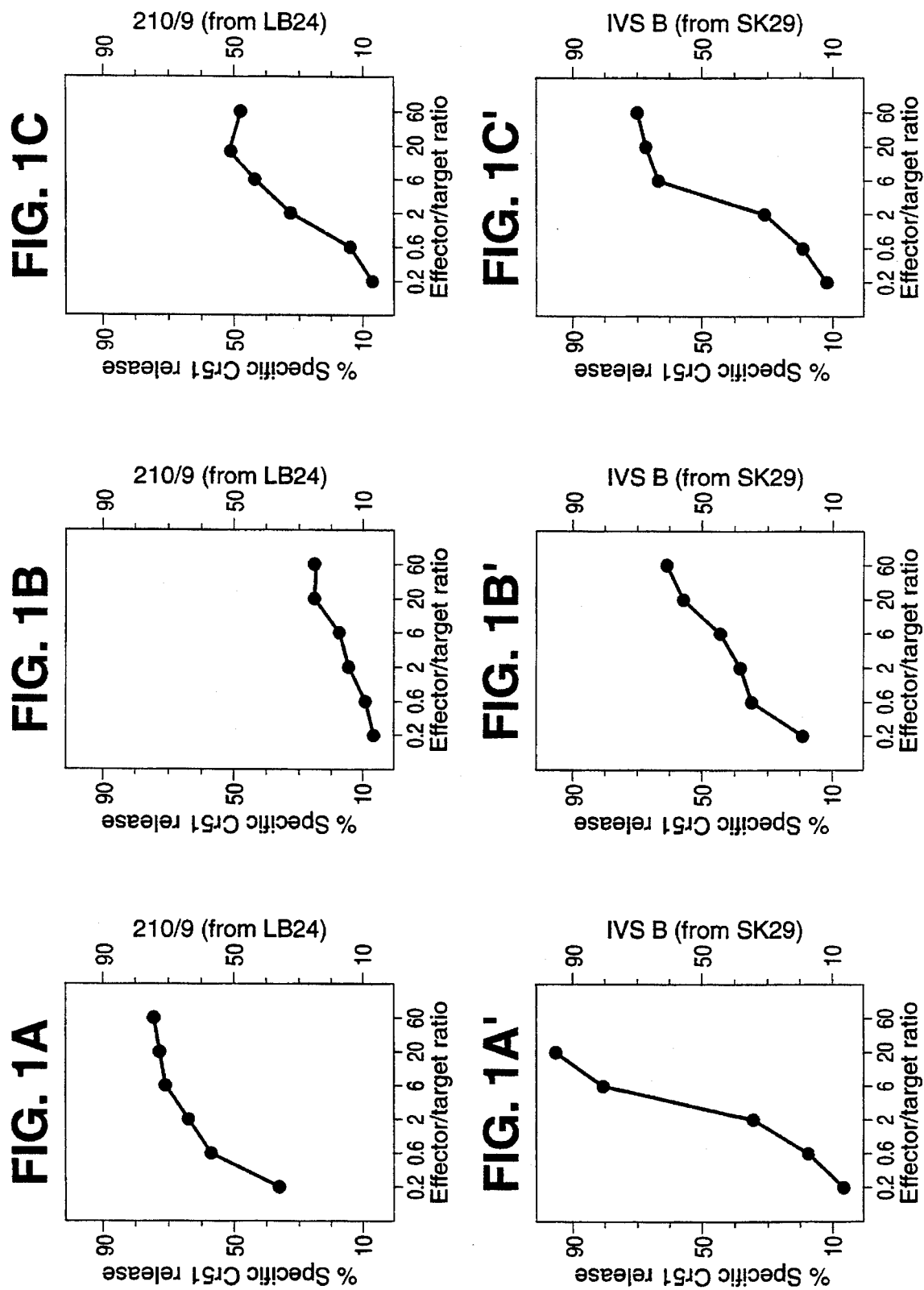

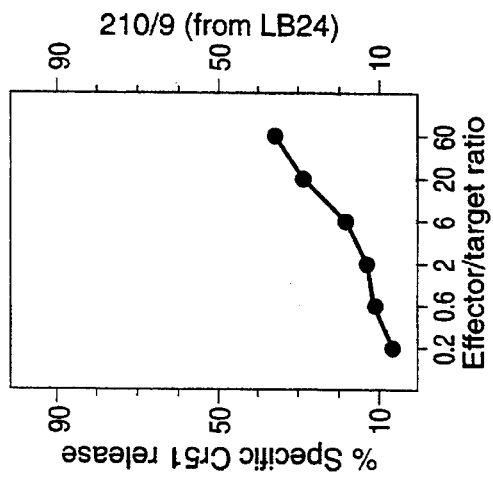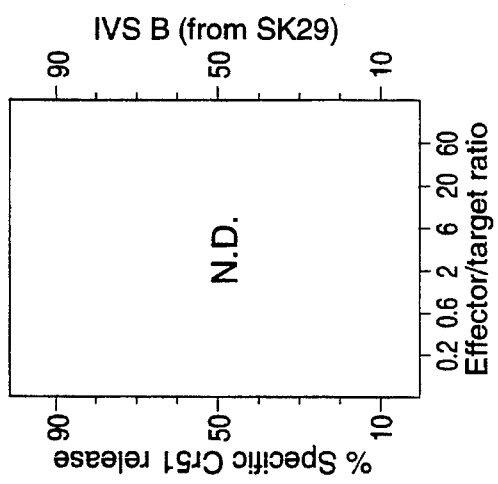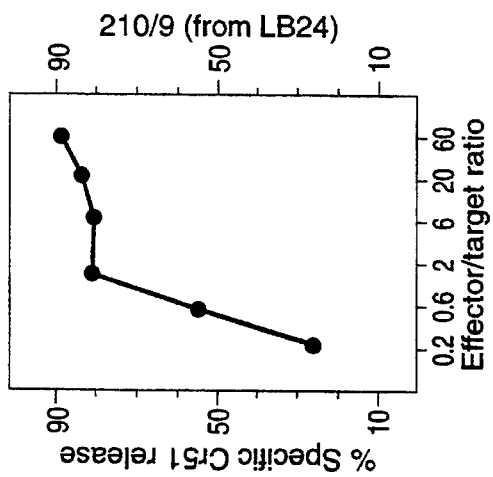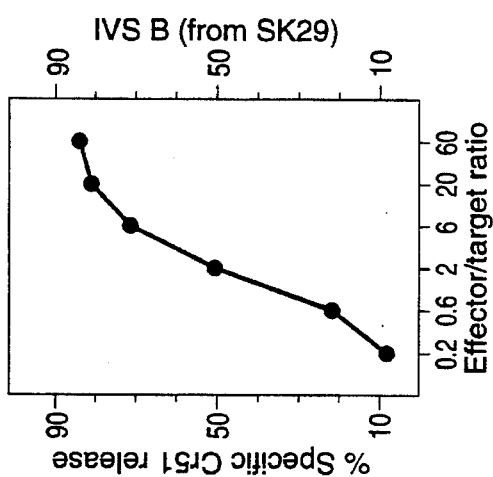

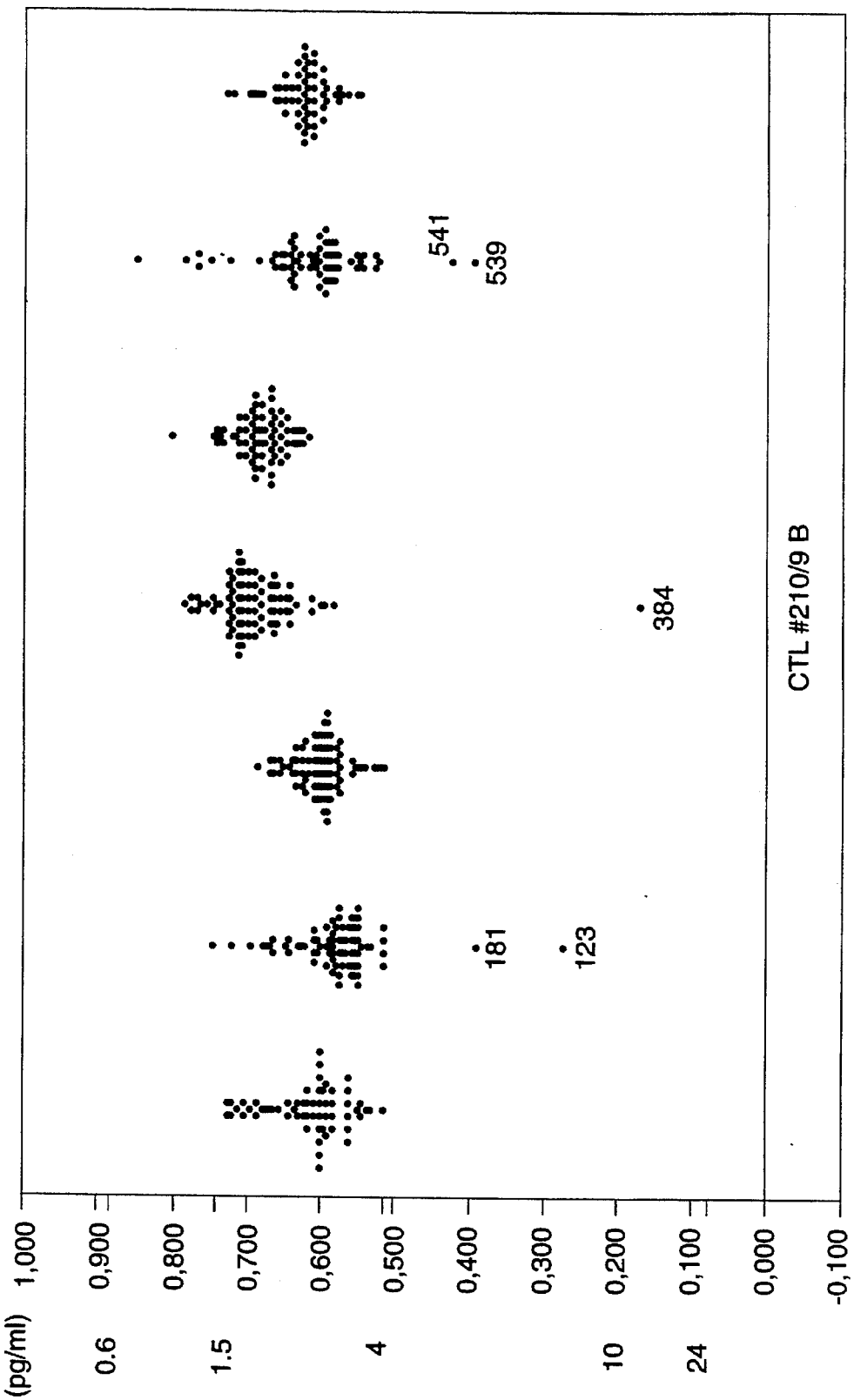

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 1894 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GGA  AGA  ATG  CTC  CTG  GCT  GTT  TTG  TAC  TGC  CTG  CTG  TGG  AGT  TTC  CAG         48
Gly  Arg  Met  Leu  Leu  Ala  Val  Leu  Tyr  Cys  Leu  Leu  Trp  Ser  Phe  Gln
              -15                      -10                       -5

ACC  TCC  GCT  GGC  CAT  TTC  CCT  AGA  GCC  TGT  GTC  TCC  TCT  AAG  AAC  CTG         96
Thr  Ser  Ala  Gly  His  Phe  Pro  Arg  Ala  Cys  Val  Ser  Ser  Lys  Asn  Leu
                1              5                      10

ATG  GAG  AAG  GAA  TGC  TGT  CCA  CCG  TGG  AGC  GGG  GAC  AGG  AGT  CCC  TGT        144
Met  Glu  Lys  Glu  Cys  Cys  Pro  Pro  Trp  Ser  Gly  Asp  Arg  Ser  Pro  Cys
 15                      20                       25                       30

GGC  CAG  CTT  TCA  GGC  AGA  GGT  TCC  TGT  CAG  AAT  ATC  CTT  CTG  TCC  AAT        192
Gly  Gln  Leu  Ser  Gly  Arg  Gly  Ser  Cys  Gln  Asn  Ile  Leu  Leu  Ser  Asn
```

-continued

| | | | | | | | | | | | | | | | | |
|---|---|---|---|---|---|---|---|---|---|---|---|---|---|---|---|---|
| | | | 35 | | | | | 40 | | | | | 45 | | | |
| GCA | CCA | CTT | GGG | CCT | CAA | TTT | CCC | TTC | ACA | GGG | GTG | GAT | GAC | CGG | GAG | 240 |
| Ala | Pro | Leu | Gly 50 | Pro | Gln | Phe | Pro | Phe 55 | Thr | Gly | Val | Asp | Asp 60 | Arg | Glu | |
| TCG | TGG | CCT | TCC | GTC | TTT | TAT | AAT | AGG | ACC | TGC | CAG | TGC | TCT | GGC | AAC | 288 |
| Ser | Trp | Pro 65 | Ser | Val | Phe | Tyr | Asn 70 | Arg | Thr | Cys | Gln | Cys 75 | Ser | Gly | Asn | |
| TTC | ATG | GGA | TTC | AAC | TGT | GGA | AAC | TGC | AAG | TTT | GGC | TTT | TGG | GGA | CCA | 336 |
| Phe | Met 80 | Gly | Phe | Asn | Cys | Gly | Asn 85 | Cys | Lys | Phe | Gly 90 | Phe | Trp | Gly | Pro | |
| AAC | TGC | ACA | GAG | AGA | CGA | CTC | TTG | GTG | AGA | AGA | AAC | ATC | TTC | GAT | TTG | 384 |
| Asn 95 | Cys | Thr | Glu | Arg 100 | Arg | Leu | Leu | Val | Arg 105 | Arg | Asn | Ile | Phe | Asp 110 | Leu | |
| AGT | GCC | CCA | GAG | AAG | GAC | AAA | TTT | TTT | GCC | TAC | CTC | ACT | TTA | GCA | AAG | 432 |
| Ser | Ala | Pro | Glu | Lys 115 | Asp | Lys | Phe | Phe | Ala 120 | Tyr | Leu | Thr | Leu | Ala 125 | Lys | |
| CAT | ACC | ATC | AGC | TCA | GAC | TAT | GTC | ATC | CCC | ATA | GGG | ACC | TAT | GGC | CAA | 480 |
| His | Thr | Ile | Ser 130 | Ser | Asp | Tyr | Val | Ile 135 | Pro | Ile | Gly | Thr | Tyr 140 | Gly | Gln | |
| ATG | AAA | AAT | GGA | TCA | ACA | CCC | ATG | TTT | AAC | GAC | ATC | AAT | ATT | TAT | GAC | 528 |
| Met | Lys | Asn 145 | Gly | Ser | Thr | Pro | Met 150 | Phe | Asn | Asp | Ile | Asn 155 | Ile | Tyr | Asp | |
| CTC | TTT | GTC | TGG | ATG | CAT | TAT | TAT | GTG | TCA | ATG | GAT | GCA | CTG | CTT | GGG | 576 |
| Leu | Phe 160 | Val | Trp | Ile | His | Tyr 165 | Tyr | Val | Ser | Met | Asp 170 | Ala | Leu | Leu | Gly | |
| GGA | TCT | GAA | ATC | TGG | AGA | GAC | ATT | GAT | TTT | GCC | CAT | GAA | GCA | CCA | GCT | 624 |
| Gly 175 | Tyr | Glu | Ile | Trp | Arg 180 | Asp | Ile | Asp | Phe | Ala 185 | His | Glu | Ala | Pro | Ala 190 | |
| TTT | CTG | CCT | TGG | CAT | AGA | CTC | TTC | TTG | TTG | CGG | TGG | GAA | CAA | GAA | ATC | 672 |
| Phe | Leu | Pro | Trp | His 195 | Arg | Leu | Phe | Leu | Arg 200 | Trp | Glu | Gln | Glu | Ile 205 | | |
| CAG | AAG | CTG | ACA | GGA | GAT | GAA | AAC | TTC | ACT | ATT | CCA | TAT | TGG | GAC | TGG | 720 |
| Gln | Lys | Leu | Thr 210 | Gly | Asp | Gly | Asn | Phe 215 | Thr | Ile | Pro | Tyr | Trp 220 | Asp | Trp | |
| CGG | GAT | GCA | GAA | AAG | TGT | GAC | ATT | TGC | ACA | GAT | GAG | TAC | ATG | GGA | GGT | 768 |
| Arg | Asp | Ala 225 | Glu | Lys | Cys | Asp | Ile 230 | Cys | Thr | Asp | Gly | Tyr 235 | Met | Gly | Gly | |
| CAG | CAC | CCC | ACA | AAT | CCT | AAC | TTA | CTC | AGC | CCA | GCA | TCA | TTC | TTC | TCC | 816 |
| Gln | His 240 | Pro | Thr | Asn | Pro | Asn 245 | Leu | Leu | Ser | Pro | Ala 250 | Ser | Phe | Phe | Ser | |
| TCT | TGG | CAG | ATT | GTC | TGT | AGC | CGA | TTG | GAG | GAG | TAC | AAC | AGC | CAT | CAG | 864 |
| Ser | Trp 255 | Gln | Ile | Val | Cys | Ser 260 | Arg | Leu | Glu | Glu | Tyr 265 | Asn | Ser | His | Gln 270 | |
| TCT | TTA | TGC | AAT | GGA | ACG | CCC | GAG | GGA | CCT | TTA | CGG | CGT | AAT | CCT | GGA | 912 |
| Ser | Leu | Cys | Asn | Gly 275 | Thr | Pro | Glu | Gly | Pro 280 | Leu | Arg | Arg | Asn | Pro 285 | Gly | |
| AAC | CAT | GAC | AAA | TCC | AGA | ACC | CCA | AGG | CTC | CCC | TCT | TCA | GCT | GAT | GTA | 960 |
| Asn | His | Asp | Lys 290 | Ser | Arg | Thr | Pro | Arg 295 | Leu | Pro | Ser | Ser | Ala 300 | Asp | Val | |
| GAA | TTT | TGC | CTG | AGT | TTG | ACC | CAA | TAT | GAA | TCT | GGT | TCC | ATG | GAT | AAA | 1008 |
| Glu | Phe | Cys 305 | Leu | Ser | Leu | Thr | Gln 310 | Tyr | Glu | Ser | Gly | Ser 315 | Met | Asp | Lys | |
| GCT | GCC | AAT | TTC | AGC | TTT | AGA | AAT | ACA | CTG | GAA | GGA | TTT | GCT | AGT | CCA | 1056 |
| Ala | Ala | Asn | Phe 320 | Ser | Phe | Arg | Asn | Thr 325 | Leu | Glu | Gly | Phe | Ala 330 | Ser | Pro | |
| CTT | ACT | GGG | ATA | GCG | GAT | GCC | TCT | CAA | AGC | AGC | ATG | CAC | AAT | GCC | TTG | 1104 |
| Leu | Thr | Gly | Ile | Ala 340 | Asp | Ala | Ser | Gln | Ser 345 | Ser | Met | His | Asn | Ala 350 | Leu | |
| CAC | ATC | TAT | ATG | AAT | GGA | ACA | ATG | TCC | CAG | GTA | CAG | GGA | TCT | GCC | AAC | 1152 |
| His | Ile | Tyr | Met | Asn | Gly | Thr | Met | Ser | Gln | Met | Gln | Gly | Ser | Ala | Asn | |

335

|   |   |   |   |   |   |   | 355 |   |   |   |   | 360 |   |   |   |   | 365 |   |   |      |
|---|---|---|---|---|---|---|---|---|---|---|---|---|---|---|---|---|---|---|---|------|

GAT CCT ATC TTC CTT CTT CAC CAT GCA TTT GTT GAC AGT ATT TTT GAG 1200
Asp Pro Ile Phe Leu Leu His His Ala Phe Val Asp Ser Ile Phe Glu
        370                     375                 380

CAG TGG CTC CAA AGG CAC CGT CCT CTT CAA GAA GTT TAT CCA GAA GCC 1248
Gln Trp Leu Arg Arg His Arg Pro Leu Gln Glu Val Tyr Pro Glu Ala
            385                     390                 395

AAT GCA CCC ATT GGA CAT AAC CGG GAA TCC TAC ATG GTT CCT TTT ATA 1296
Asn Ala Pro Ile Gly His Asn Arg Glu Ser Tyr Met Val Pro Phe Ile
    400                     405                 410

CCA CTG TAC AGA AAT GGT GAT TTC TTT ATT TCA TCC AAA GAT CTG GGC 1344
Pro Leu Tyr Arg Asn Gly Asp Phe Phe Ile Ser Ser Lys Asp Leu Gly
415                 420                     425                 430

TAT GAC TAT AGC TAT CTA CAA GAT TCA GAC CCA GAC TCT TTT CAA GAC 1392
Tyr Asp Tyr Ser Tyr Leu Gln Asp Ser Asp Pro Asp Ser Phe Gln Asp
            435                     440                 445

TAC ATT AAG TCC TAT TTG GAA CAA GCG AGT CGG ATC TGG TCA TGG CTC 1440
Tyr Ile Lys Ser Tyr Leu Gly Gln Ala Ser Arg Ile Trp Ser Trp Leu
                450                 455                 460

CTT GGG GCG GCG ATG GTA GGG GCC GTC CTC ACT GCC CTG CTG GCA GGG 1488
Leu Gly Ala Ala Met Val Gly Ala Val Leu Thr Ala Leu Leu Ala Gly
            465                     470                 475

CTT GTG AGC TTG CTG TGT CGT CAC AAG AGA AAG CAG CTT CCT GAA GAA 1536
Leu Val Ser Leu Leu Cys Arg His Lys Arg Lys Gln Leu Pro Glu Glu
    480                     485                 490

AAG CAG CCA CTC CTC ATG GAG AAA GAG GAT TAC CAC AGC TTG TAT CAG 1584
Lys Gln Pro Leu Leu Met Glu Lys Glu Asp Tyr His Ser Leu Tyr Gln
495                 500                     505                 510

AGC CAT TTA                                                       1593
Ser His Leu
        513

TAAAAGGCTT AGGCAATAGA GTAGGGCCAA AAAGCCTGAC CTCACTCTAA CTCAAAGTAA 1653

TGTCCAGGTT CCCAGAGAAT ATCTGCTGGT ATTTTCTGT AAAGACCATT TGCAAAATTG 1713

TAACCTAATA CAAAGTGTAG CCTTCTTCCA ACTCAGGTAG AACACACCTG TCTTTGTCTT 1773

GCTGTTTTCA CTCAGCCCTT TTAACATTTT CCCCTAAGCC CATATGTCTA AGGAAAGGAT 1833

GCTATTTGGT AATGAGGAAC TGTTATTTGT ATGTGAATTA AAGTGCTCTT ATTTTAAAAA 1893

A                                                                    1894

( 2 ) INFORMATION FOR SEQ ID NO: 2:

( i ) SEQUENCE CHARACTERISTICS:
            ( A ) LENGTH: 9 amino acid residues
            ( B ) TYPE: amino acid
            ( D ) TOPOLOGY: linear ( x i ) SEQUENCE DESCRIPTION: SEQ ID NO: 2:

Tyr Met Asn Gly Thr Met Ser Gln Val
5

( 2 ) INFORMATION FOR SEQ ID NO: 3:

( i ) SEQUENCE CHARACTERISTICS:
            ( A ) LENGTH: 10 amino acid residues
            ( B ) TYPE: amino acid
            ( D ) TOPOLOGY: linear ( x i ) SEQUENCE DESCRIPTION: SEQ ID NO: 3:

Met Leu Leu Ala Val Leu Tyr Cys Leu Leu
5                   10

(2) INFORMATION FOR SEQ ID NO: 4:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 4:

Met Leu Leu Ala Val Leu Tyr Cys Leu
5

(2) INFORMATION FOR SEQ ID NO: 5:

(i) SEQUENCE CHARACTERISTICS:
        (A) LENGTH: 9 amino acid residues
        (B) TYPE: amino acid
        (D) TOPOLOGY: linear (xi) SEQUENCE DESCRIPTION: SEQ ID NO: 5:

Leu Leu Ala Val Leu Tyr Cys Leu Leu
5

ISOLATED, TYROSINASE DERIVED PEPTIDES AND USES THEREOF

RELATED APPLICATION

This application is a continuation-in-part of application Ser. No. 08/081,673, filed Jun. 23, 1993 U.S. Pat. No. 5,487,944 which is a continuation in part of U.S. patent application Ser. No. 054,714, filed Apr. 28, 1993 which is a continuation-in-part of U.S. patent application Ser. No. 994,928, filed Dec. 22, 1992, now abandoned.

FIELD OF THE INVENTION

This invention relates to isolated peptides derived from tyrosinase which are presented by HLA-A2 molecules, and uses thereof. In addition, it relates to the ability to identify those individuals diagnosed with conditions characterized by cellular abnormalities whose abnormal cells present complexes of these peptides and HLA-A2, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257:919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35:145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBO J 7:2715 (1988)). An early report of cDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application 08/081,673, filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules.

BRIEF DESCRIPTION OF THE FIGURES

FIG. 1 describes, collectively, cell lysis studies. In particular:

FIG. 1A shows lysis of cell line LB24-MEL;

FIG. 1B shows lysis of cell line SK29-MEL;

FIG. 1C shows lysis of cell line LB4.MEL;

FIG. 1D shows lysis of cell line SK23.MEL;

FIG. 1E shows lysis of cell line LE516.MEL;

FIG. 1J shows lysis of autologous EBV transformed B cells from patient SK29.

FIG. 3 depicts studies of TNF release of CTL 210/9.

In FIG. 7, the symbol "0" is used for cell line T2, "■" for MZ2-MEL not presenting HLA-A2, and "●" for MZ2-MEL which has been transfected to present HLA-A2. Example 12 elaborates on these tests.

DETAILED DESCRIPTION OF PREFERRED EMBODIMENTS

EXAMPLE 1

Figure 1F:
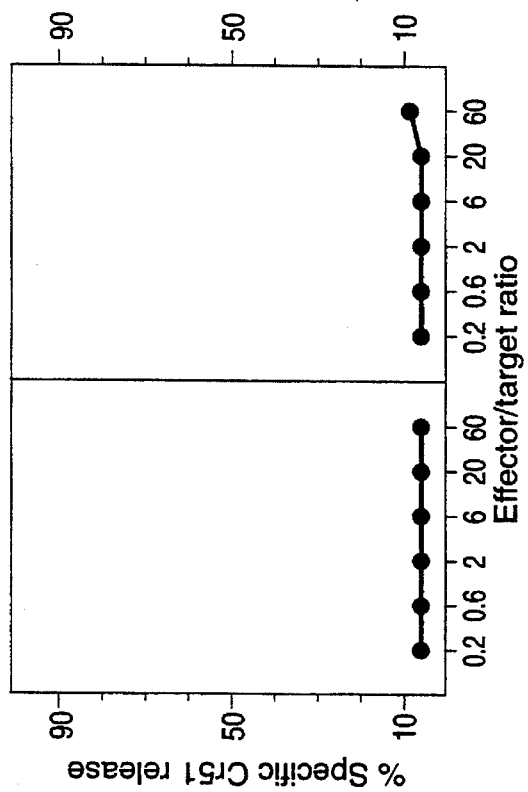
FIG. 1F shows lysis of cell line SK29-MEL.1.22 which has lost HLA-A2 expression.
Figure 1F:
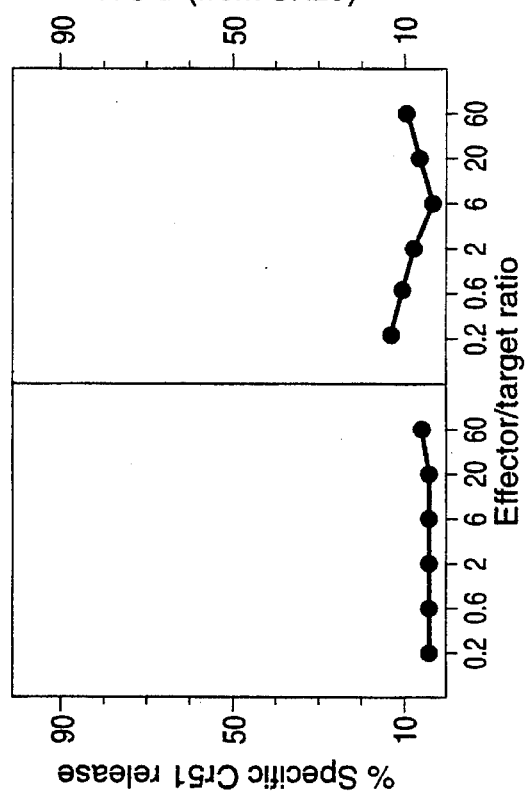
Figure 1I:
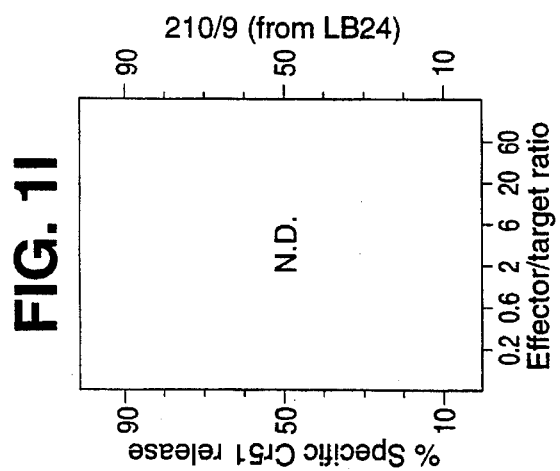
FIG. 1I shows lysis of the loss variant in FIG. 1F after transfection with a gene for HLA-A2.
Figure 1I:
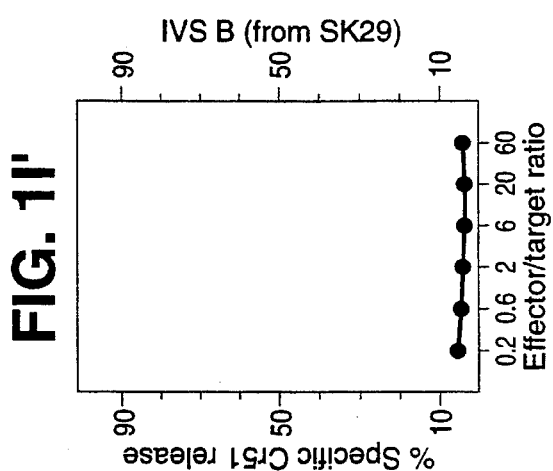
Figure 1H:
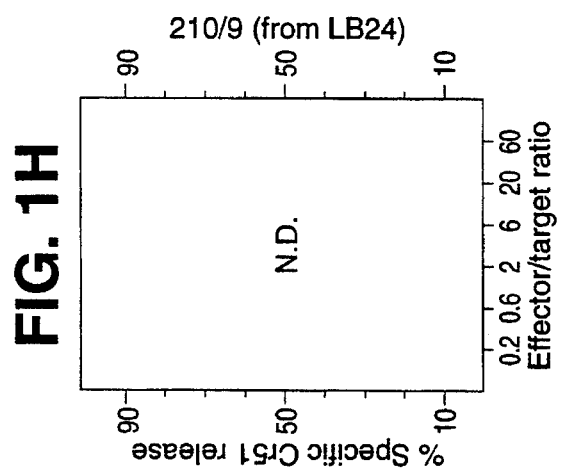
FIG. 1H shows lysis studies on NK target K562.
Figure 1H:
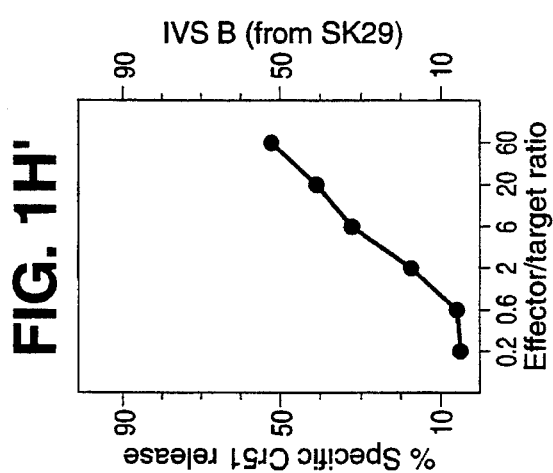
Figure 1G:
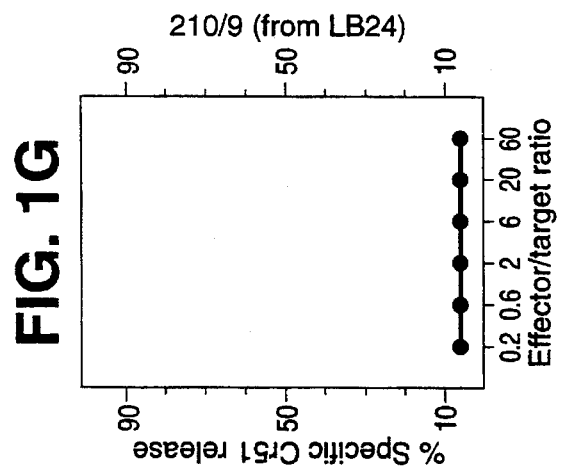
FIG. 1G shows lack of lysis of MZ2-MEL.
Figure 1G:
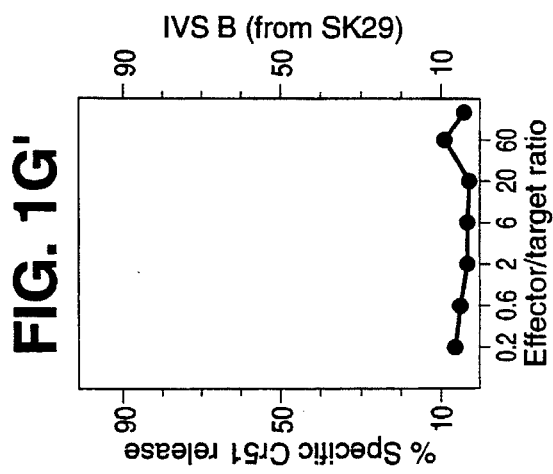

Melanoma cell lines SK 29-MEL (also referred to in the literature as SK MEL-29) and LB24-MEL, which have been available to researchers for many years, were used in the following experiments.

Samples containing mononuclear blood cells were taken from patients SK29 (AV) and LB2 (these patients were also the source of SK 29-MEL and LB24-MEL, respectively). The melanoma cell lines were contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 μCi/ml of Na($^{51}$Cr)O$_4$. Labelled cells were washed three times with DMEM, supplemented with 10 mMHepes. These were then resuspended in DMEM supplemented with 10 mMHepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of CO$_2$ atmosphere.

Plates were centrifuged again, and 100 ul aliquots of supernatant were collected and counted. Percentage of $^{51}$Cr release was calculated as follows:

$$\% \ ^{51}Cr\ release = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-transformed B cells (EBV-B cells) were used, the only change was the replacement of DMEM medium by Hank's medium, supplemented with 5% FCS.

These experiments led to isolation of CTL clone "IVSB" from patient SK29 (AV) and CTL clone 210/9 from patient LB24.

FIG. 1 presents the results of these assays, in panels A, B, G and I. Specifically, it will be seen that both CTLs lysed both melanoma cell lines, and that there was no lysis of the K562 and EBV-B cell lines.

EXAMPLE 2

The CTLs described were tested against other melanoma cell lines to determine whether their target was shared by other melanoma cell lines. Lysis as described in Example 1 was studied for lines LB4.MEL, SK23.MEL (also known as SK MEL-23), and LE516.MEL. FIG. 1, panels C, D and E shows that the clones did lyse these lines.

The tested lines are known to be of type HLA-A2, and the results suggested that the CTLs are specific for a complex of peptide and HLA-A2. This suggestion was verified by testing a variant of SK 29-MEL which has lost HLA-A2 expression. FIG. 1, panel F shows these results. Neither clone lysed the HLA-loss variant. When the variant was transfected with the HLA-A2 gene of SK29-MEL, however, and retested, lysis was observed. Thus, it can be concluded that the presenting molecule is HLA-A2.

EXAMPLE 3

Once the presenting HLA molecule was identified, studies were carried out to identify the molecule, referred to hereafter as the "tumor rejection antigen precursor" or "TRAP" molecule which was the source of the presented peptide.

To do this, total RNA was isolated from cell line SK29-MEL.1, which is a subclone of SK29-MEL. The RNA was isolated using an oligo-dT binding kit, following well recognized techniques. Once the total RNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 E. coli (electroporation conditions: 1 pulse at 25 μfarads, 2500 V).

The transfected bacteria were selected with ampicillin (50 μg/ml), and then divided into 700 pools of 200 clones each. Each pool represented about 100 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

EXAMPLE 4

The amplified plasmids were then transfected into eukaryotic cells. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, 100 ng of plasmid pcDNA-I/Amp-A 2 and 100 ng of DNA of a pool of the cDNA library described supra. Plasmid pcDNA-I/Amp-A2 contains the HLA-A2 gene from SK29MEL. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of either of the described CTL clones were added, in 100 μl of Iscove medium containing 10% pooled human serum. When clone 210/9 was used, the medium was supplemented with 25 U/ml of IL-2. Supernatant was removed after 24 hours, and TNF content was determined in an assay on WEHI cells, as described by Traversari et al., Immunogenetics 35:145–152 (1992), the disclosure of which is incorporated by reference.

Figure 2:
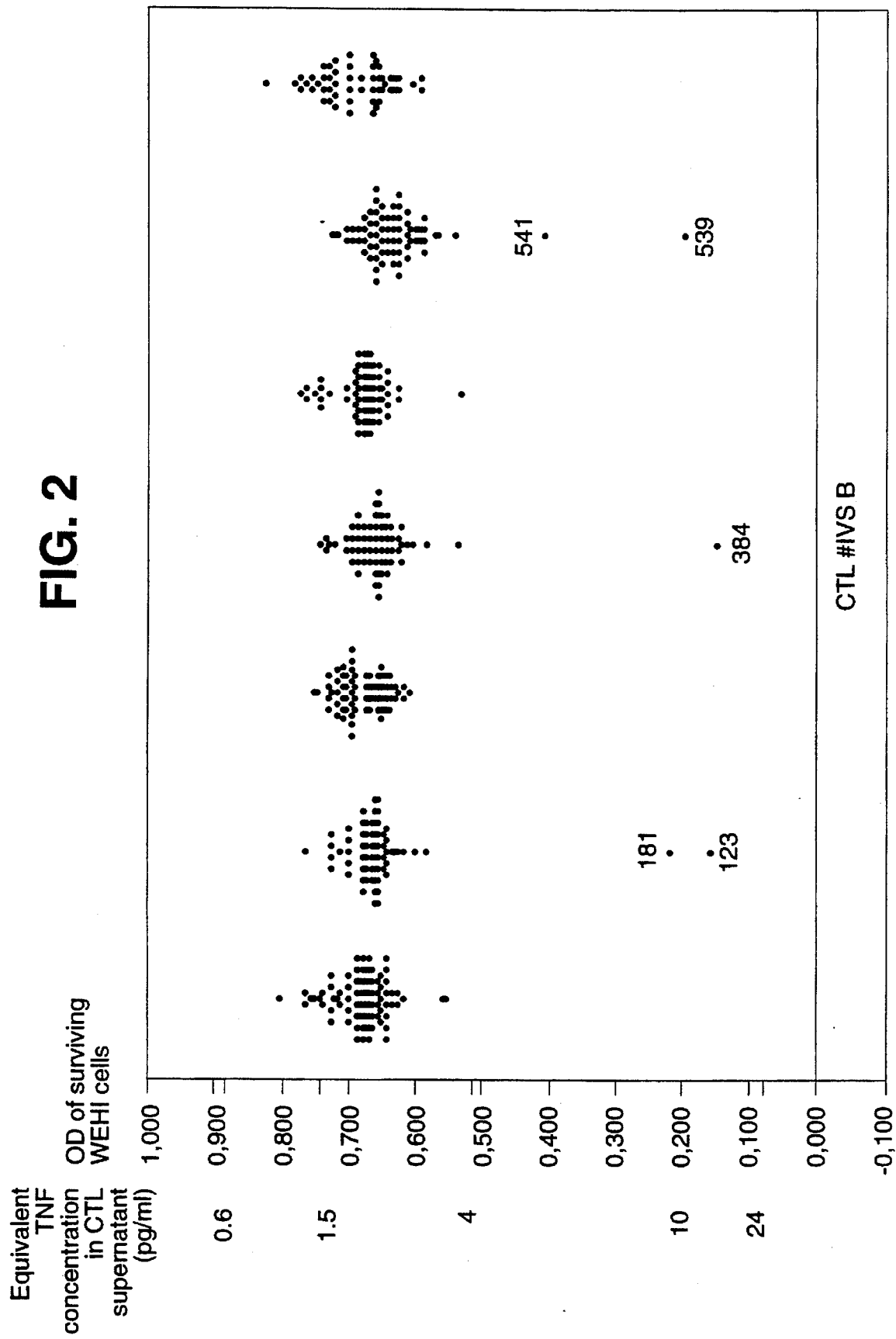
FIG. 2 presents studies of TNF release of CTL IVSB.

Of 700 wells tested with IVSB, 696 showed between 0.6 and 4 pg of TNF per ml. The remaining four wells contained between 10 and 20 pg/ml of TNF. Homologous wells tested with CTL 210/9 showed similar, clearly higher values. FIGS. 2 and 3 present these data.

EXAMPLE 5

Three of the four pools identified as high producers (numbers "123", "181" and "384") were selected for further experiments. Specifically, the bacteria were cloned, and 570 bacteria were tested from each pool. Plasmid DNA was extracted therefrom, transfected into a new sample of COS cells in the same manner as described supra, and the cells were again tested for stimulation of CTL 210/9 and CTL IVSB. A positive clone was found in pool 123 ("p123.B2"), and one was found in pool 384 ("p384.C6"). Convincing evidence that the transfected cells were recognized by CTLs was obtained by carrying out a comparative test of COS cells transfected with cDNA and the HLA-A2 gene, and COS cells transfected only with HLA-A2. TNF release in CTL supernatant was measured by testing it on WEHI cells. The optical density of the surviving WEHI cells was measured using MTT. Results are presented in Table 1:

TABLE 1

|       | cDNA (123.B2) + HLA-A2 DNA | no cDNA + HLA-A2 |
|-------|---------------------------|------------------|
| Run 1 | 0.087                     | 0.502            |
| Run 2 | 0.108                     | 0.562            |

The values for WEHI OD's correspond to 24 pg/ml of TNF for cDNA and HLA-A2, versus 2.3 pg/ml for the control.

The plasmids from the positive clones were removed, and sequenced following art known techniques. A sequence search revealed that the plasmid insert was nearly identical to the cDNA for human tyrosinase, as described by Bouchard et al., J. Exp. Med. 169: 2029 (1989), the disclosure of which is incorporated by reference. Thus, a normally occurring molecule (i.e., tyrosinase), may act as a tumor rejection antigen precursor and be processed to form a peptide tumor rejection antigen which is presented on the surface of a cell, in combination with HLA-A2, thereby stimulating lysis by CTL clones. The nucleic sequence of the identified molecule is presented as SEQ ID NO: 1.

EXAMPLE 6

Prior work reported by Chomez et al., Immunogenetics 35:241 (1992) has shown that small gene fragments which contain a sequence coding for an antigenic peptide resulted in expression of that peptide. This work, which is incorporated by reference in its entirety, suggested the cloning of small portions of the human tyrosinase cDNA described supra and in SEQ ID NO: 1. Using the methodologies described in examples 1–5, various fragments of the cDNA were cotransfected with a gene for HLA-A2 in COS-7 cells, and TNF release assays were performed. These experiments led to identification of an approximately 400 base pair fragment which, when used in cotransfection experiments, provoked TNF release from cytolytic T cell clone CTL IVSB discussed supra, shown to be specific for HLA-A2 presenting cells. The 400 base fragment used corresponded to bases 711 to 1152 of SEQ ID NO: 1. The amino acid sequence for which the fragment codes was deduced, and this sequence was then compared to the information provided by Hunt et al., Science 255: 1261 (1992), and Falk et al., Nature 351: 290 (1991), the disclosures of which are both incorporated by reference in their entirety. These references discuss consensus sequences for HLA-A2 presented peptides. Specifically, Hunt discusses nonapeptides, where either Leu or Ile is always found at the second position, Leu being the "dominant residue". The ninth residue is described as always being a residue with an aliphatic hydrocarbon side chain. Val is the dominant residue at this position. Hunt, discusses a strong signal for Leu and an intermediate signal for Met at the second position, one of Val, Leu, Ile or Thr at position 6, and Val or Leu at position 9, with Val being particularly strong. On the basis of the comparison, nonapeptides were synthesized and then tested to see if they could sensitize HLA-A 2 presenting cells. To do so, tyrosinase loss variant cell lines SK29-MEL 1.218 and T202LB were used. Varying concentrations of the tested peptides were added to the cell lines, together with either of cytolytic T cell clone CTL IVSB or cytolytic T cell clone CTL 2/9. Prior work, described supra, had established that the former clone lysed tyrosinase expressing cells which present HLA-A2, and that the latter did not.

The tyrosinase loss variants were incubated for one hour in a solution containing $^{51}Cr$, at 37° C., either with or without anti HLA-A2 antibody MA2.1, which was used to stabilize empty HLA-A2 molecules. In the tests, cells were washed four times, and then incubated with varying dilutions of the peptides, from 100 μM down to 0.01 μM. After 30 minutes, effector cells were added at an E/T ratio of 40/1 and four hours later, 100λ of supernatant were collected and radioactivity counted.

Figure 4A:
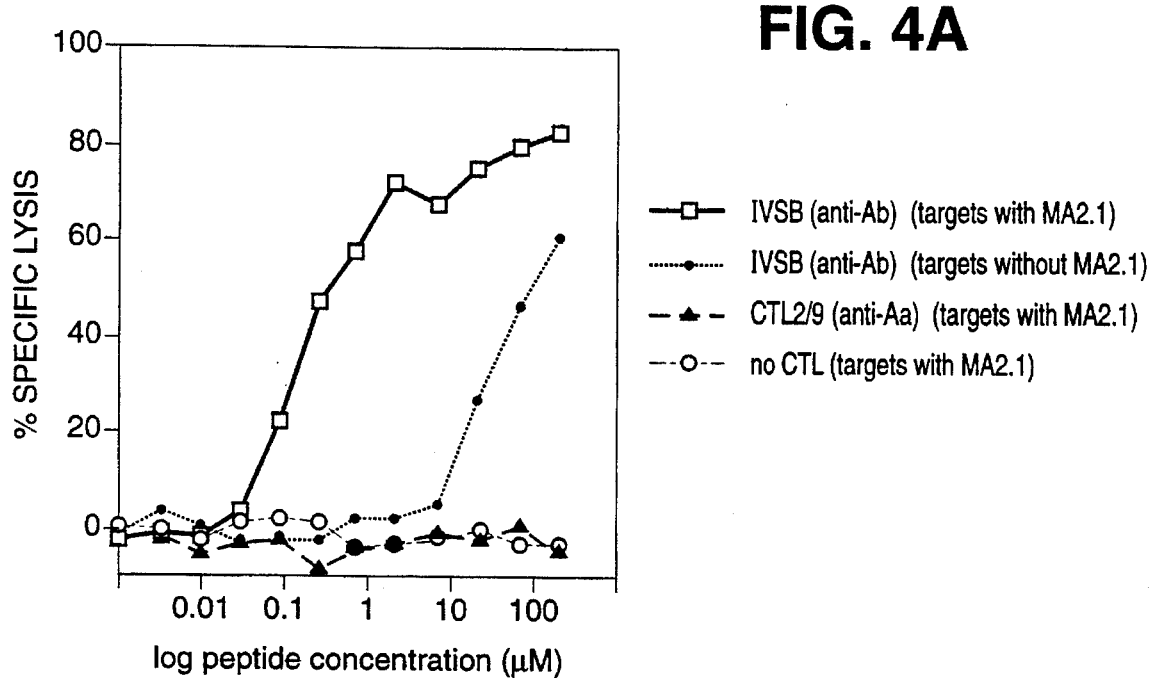
FIG. 4 depicts the recognition of the peptide YMNGTMSQV by cytolytic T cell clone CTL-IVSB but not cytolytic T cell clone CTL 2/9.
Figure 4B:
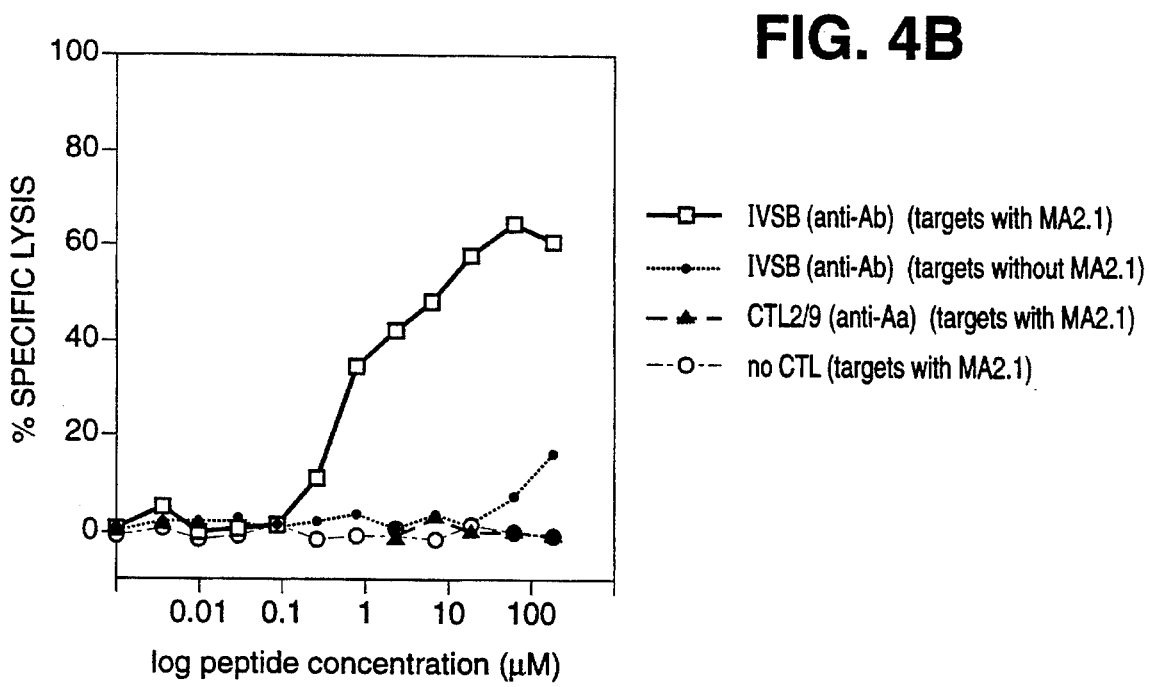
Figure 5:
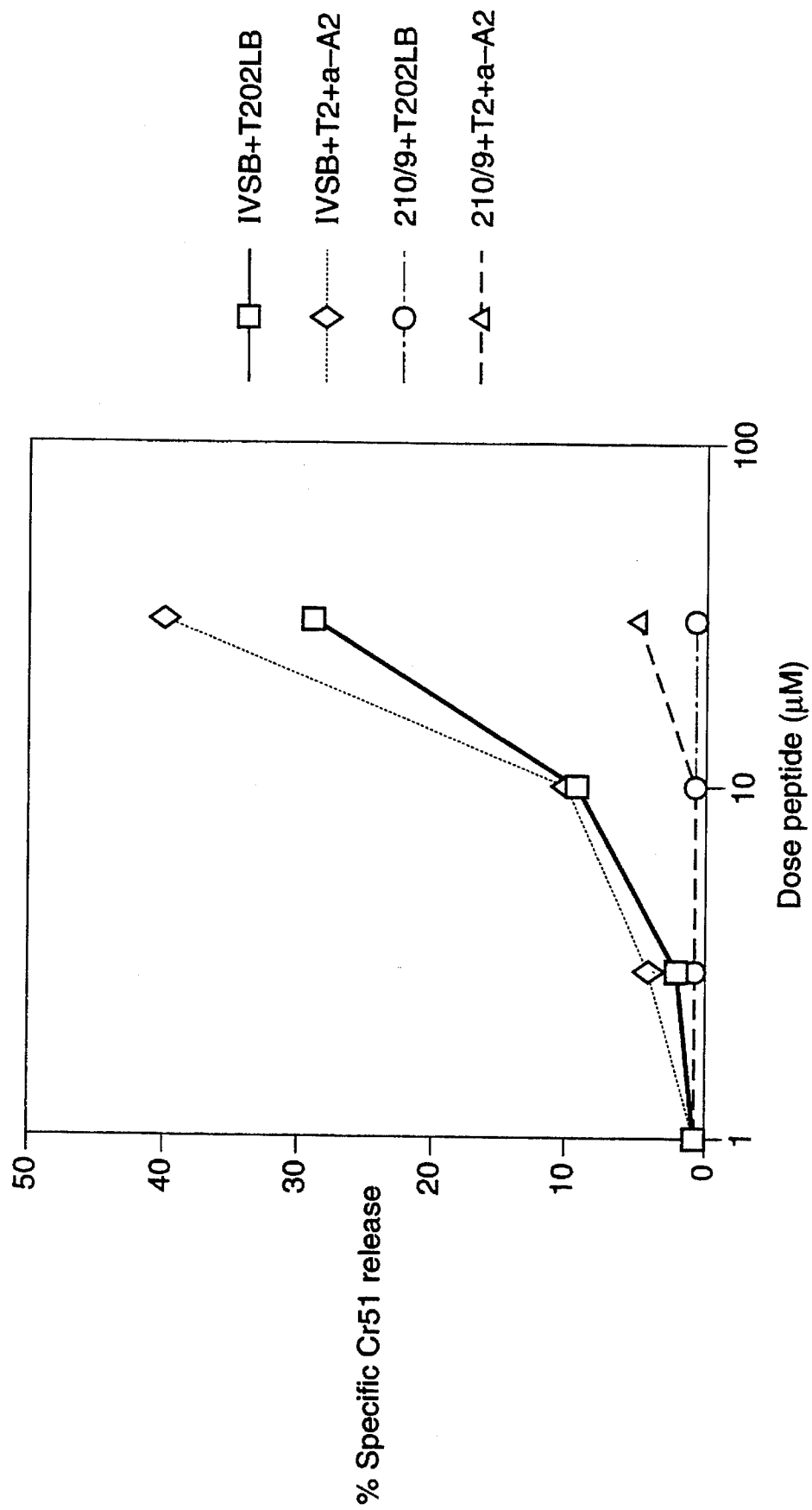
FIG. 5 shows that the peptide YMNGTMSQV is not recognized by cytolytic T cell clone CTL 210/9.

FIG. 4 shows the results obtained with nonapeptide

Tyr Met Asn Gly Thr Met Ser Gln Val        (SEQ ID NO: 2).

This peptide, referred to hereafter as SEQ ID NO: 2, corresponds to residues 1129-1155 of the cDNA sequence for tyrosinase presented in SEQ ID NO: 1. Complexes of HLA-A2 and this peptide are recognized by CTL clone IVSB.

In a parallel experiment, it was shown that CTL clone CTL 210/9, derived from patient LB24, did not recognize the complexes of HLA-A2 and the peptide of SEQ ID NO: 2, although it did recognize complexes of HLA-A2 and a tyrosinase derived peptide. Thus, tyrosinase is processed to at least one additional peptide which, when presented by HLA-A2 molecules, is recognized by CTL clones.

EXAMPLE 7

In a follow-up experiment, a second gene fragment which did not encode the peptide of SEQ ID NO: 2 was used. This fragment began at base 1 and ended at base 1101 of SEQ ID NO: 1 (i.e. the EcoRI-SphI fragment). Cytolytic T cell clone CTL 210/9, discussed supra, was tested against COS-7 cells transfected with this fragment in the manner described supra. CTL IVSB was also tested. These results, showed that LB24-CTL 210/9 recognized an antigen on the surface of HLA-A2 expressing cells transfected with this fragment, but CTL IVSB did not. Thus, a second tumor rejection antigen peptide is derived from tyrosinase.

EXAMPLE 8

In order to further define the tumor rejection antigen recognized by LB24-CTL 210/9, the following experiments were carried out.

A second fragment, corresponding to bases 451-1158 of SEQ ID NO: 1 was transfected into COS cells together with a gene for HLA-A 2, and TNF release assays were carried out. This sequence provoked TNF release from clone SK29-CTL IVSB (20 pg/ml), but not from LB24-CTL 210/9 (3.8 pg/ml). These results confirmed that the two CTL clones recognize different peptides, and that the peptide recognized by LB24-CTL 210/9 must be encoded by region 1-451.

EXAMPLE 9

The tyrosinase derived peptide coded for by cDNA fragment 1- 451 was analyzed for consensus sequences known to bind HLA-A2. The peptides corresponding to these consensus sequences were synthesized, and tested for their ability to sensitize HLA-A2 presenting cells. To do so, two tyrosinase negative melanoma cell lines were used (i.e., NA8-MEL, and MZ2-MEL 2.2 transfected with HLA-A2), and cell line T2, as described by Salter et al, Immunogenetics 21:235–246 (1985)).

The cells were incubated with $^{51}Cr$, and monoclonal antibody MA.2.1, which is specific for HLA-A2 for 50 minutes at 37° C, followed by washing (see Bodmer et al., Nature 342:443–446 (1989), the disclosure of which is incorporated by reference in its entirety). Target cells were incubated with various concentrations of the peptides, and with either of LB 24-CTL clones 210/5 or 210/9. The percent of chromium release was measured after four hours of incubation.

The peptide Met Leu Leu Ala Val Leu Tyr Cys Leu Leu (SEQ ID NO: 3) was found to be active.

In further experiments summarized here, CTL-IVSB previously shown to recognize YMNGTMSQV, did not recognize the peptide of SEQ ID NO: 3.

The results are summarized in Tables 2–4 which follow:

TABLE 2

| | PEPTIDE | |
|---|---|---|
| | YMNGTMSQV (1120–1155) | MLLAVLYCLL (25–34) |
| SK29-CTL-IVSB | + | – |
| LB24-CTL-210/5 | – | + |
| LB24-CTL-210/9 | – | + |

TABLE 3

3j95-Lysis of MZ2-2-2-A2 sensitized with tyrosiness peptides by LB24-CTL 210/5 and 210/2, and SK29-CTL IVSB

| Effectors | Peptides | Dose | MZ2.2.2.A2 + anti-A2* |
|---|---|---|---|
| LB24-CTL 210/5 (44:1) | MLLAVLYCLL (LAUS 17-5) | 10 μM<br>3<br>1 | 18<br>17<br>16 |
| | YMNGTMSQV (MAINZ) | 30 μM<br>10<br>3 | 1 |
| LB24-CTL 210/9 (30:1) | MLLAVLYCLL (LAUS 17-5) | 10 μM<br>3<br>1 | 18<br>17<br>15 |
| | YMNGTMECV (MAINZ) | 30 μM<br>10<br>8 | 1<br>1<br>1 |
| SK29-CTL N88 (40:1) | MLLAVLYCLL (LAUS 17-5) | 10 μM<br>3<br>1 | 1<br>1<br>1 |
| | YMNGTMSCV (MAINZ) | 30 μM<br>10<br>3 | 68<br>68<br>62 |

* Target cells were incubated with Cr51 and mono-Ab mA2.1 (anti-HLA-A2) for 50 min, then washed 3 times. They were incubated with various concentrations of peptides for 30 min
CTL cells were added at the indicated (E:T) ratio. The % specific CrS1 release was measured after 4 h incubation

TABLE 4

Test of tyrosinase peptides recognized by LB24-CTL 210/5 and 210/9 or SK29-CTL IVSB

| | | | (% Cr51 specific release) | | |
|---|---|---|---|---|---|
| Effectors | Peptides | Dose | NAS-MEL* | MZ2-2.2: A2 | T2 |
| LB24-CTL. 210/5 (41:1) | MLLAVLYCLL (LAUS 17-5) | 10 μM<br>3<br>1<br>300 μM<br>100<br>30<br>0 | 30<br>23<br>17<br>6<br>2<br>3<br>0 | 31<br>27<br>20<br>17<br>8<br>5<br>0 | 38<br>35<br>28<br>16<br>5<br>2<br>0 |
| LB24-CTL. 210/9 (26:1) | MLLAVLYCLL (LAUS 17-5) | 10 μM<br>3<br>1<br>300 nM<br>100<br>30 | 14<br>13<br>9<br>3<br>1<br>0 | 19<br>17<br>14<br>9<br>1<br>1 | 21<br>20<br>13<br>5<br>1<br>0 |

TABLE 4-continued

Test of tyrosinase peptides recognized by LB24-CTL 210/5 and 210/9 or SK29-CTL IVSB

| Effectors | Peptides | Dose | (% Cr51 specific release) | | |
|---|---|---|---|---|---|
| | | | NAS-MEL* | MZ2-2.2: A2 | T2 |
| | 0 | | 0 | 1 | 0 |
| SK29-CTL | YMNGTMSOV | 10 μM | 46 | 46 | 59 |
| IVSB | (MAINZ) | 3 | 38 | 44 | 52 |
| | | 1 | 27 | 40 | 46 |
| (42:1) | | 300 nM | 14 | 22 | 34 |
| | | 100 | 3 | 13 | 21 |
| | | 30 | 1 | 9 | 10 |
| | | 10 | 1 | 3 | 3 |
| | | 3 | 0 | 3 | 4 |
| | | 1 | 0 | 1 | 0 |
| | 0 | | 0 | 4 | 0 |
| spt. rel. | | | 339 | 259 | 198 |
| max-spt | | | 2694 | 1693 | 1208 |
| % | | | 11 | 13 | 14 |

EXAMPLE 10

Additional experiments were carried out using CTL clone 22/31. This clone had previously been shown to lyse subline MZ2-MEL.43 from autologous melanoma cell line MZ2-MEL, but did not lyse other sublines, such as MZ2-MEL 3.0 and MZ2-MEL 61.2, nor did it lyse autologous EBV transformed B cells, or killer cell line K562 (see Van den Eynde et al., Int. J. Cancer 44: 634–640 (1989)). The antigen presented by MZ2-MEL.43 is referred to as antigen C.

In prior work including that reported in the parent of this application, it was found that the tyrosinase gene encodes an antigen recognized by autologous CTLs on most HLA-A2 expressing melanomas. Expression of this gene in sublines of cell line MZ2-MEL was tested by PCR amplification. Clone MZ2-MEL.43 was found to be positive, whereas other MZ2-MEL clones, such as MZ2-MEL.3.0 were negative. Correlation of expression of the tyrosinase gene, and antigen MZ2-C, suggested that MZ2-C might be a tumor rejection antigen derived from tyrosinase, and presented by an HLA molecule expressed by MZ2-MEL. This cell line does not express HLA-A2, which would indicate that if a tyrosinase derived peptide were presented as a TRA, a second HLA molecule was implicated.

Figure 6:
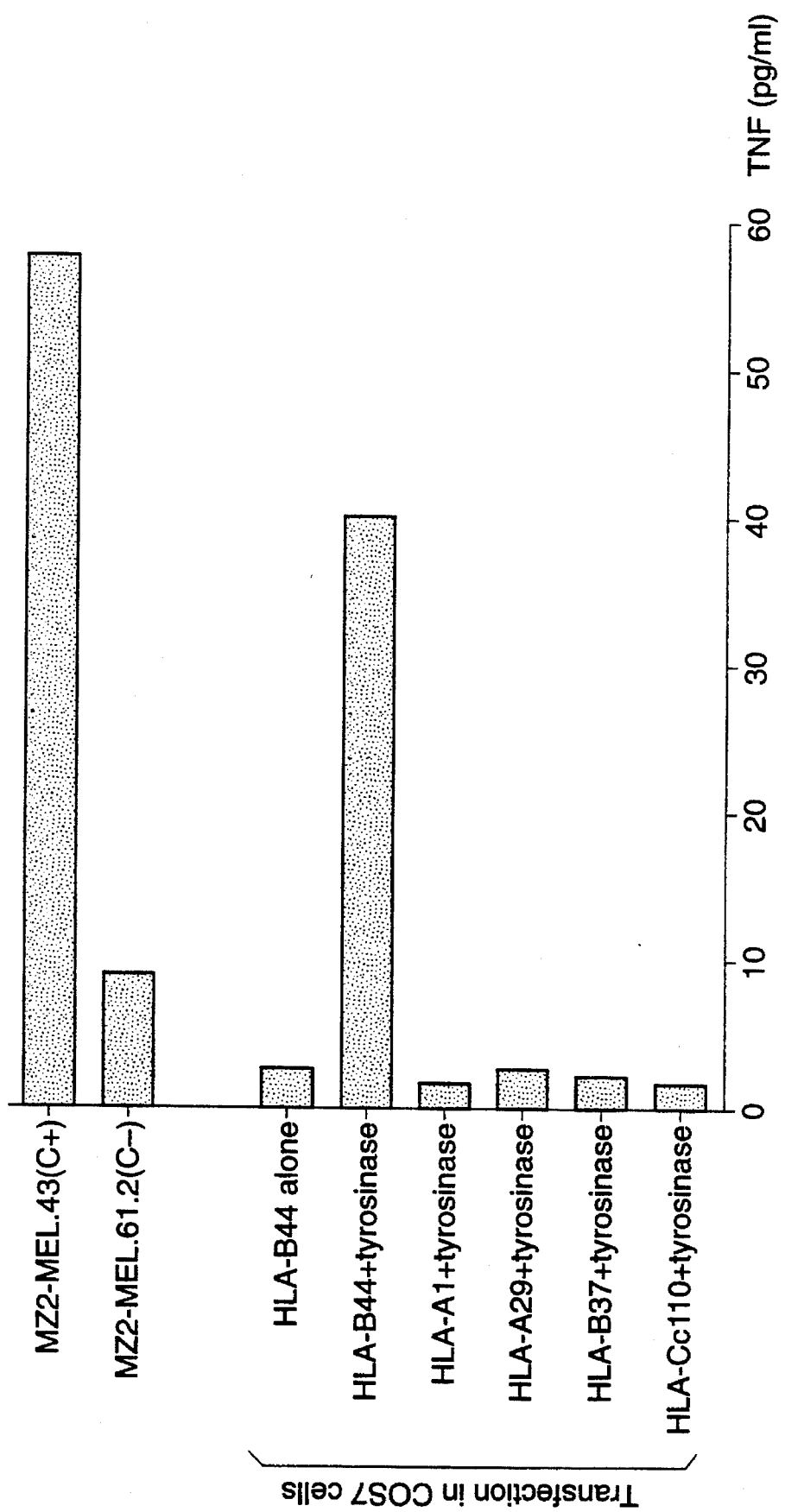
FIG. 6 shows the results obtained when TNF release assays were carried out on various cells, including those which present HLA-B 44 on their surface.

Studies were carried out to identify which HLA molecule presented antigen C to CTL 22/31. To determine this, cDNA clones of the HLA molecules known to be on the cell surface, i.e., HLA-A 29, HLA-B37, HLA-B 44.02, and HLA-C clone 10, were isolated from an MZ2-MEL.43 cDNA library, and then cloned into expression vector pcD-NAI/Amp. Recipient COS 7 cells were then transfected with one of these constructs or a construct containing HLA-A1, plus cDNA coding for tyrosinase (SEQ ID NO: 1). The contransfection followed the method set forth above. One day later CTL 22/31 was added, and 24 hours later, TNF release was measured by testing cytotoxicity on WEHI-164-13, following Traversari et al, supra. FIG. 6 shows that TNF was released by CTL 22/31 only in the presence of cells transfected with both HLA-B44 and tyrosinase. The conclusion to be drawn from this is that HLA-B44 presents a tyrosinase derived tumor rejection antigen.

EXAMPLE 11

The experiments described supra showed, inter alia, that the decamer MLLAVLYCLL effectively induced lysis of HLA-A2 presenting cells. It is fairly well accepted that MHC molecules present nonapeptides. To that end, experiments were carried out wherein two nonamers were tested, which were based upon the decapeptide which did give positive results. Specifically, either the first or tenth amino acid was omitted to create two peptides, i.e.:

Met Leu Leu Ala Val Leu Tyr Cys Leu   (SEQ ID NO: 4)

Leu Leu Ala Val Leu Tyr Cys Leu Leu   (SEQ ID NO: 5).

These peptides were tested in the same way the decapeptide was tested, as set forth in the prior examples at concentrations ranging from 10 μM to 1 nM. Three presenting cells were used. As summarized in Table 5, which follows, "T2" is a mutant human cell line, "CEMX721.174T2" as described by Salter, Immunogenetics 21: 35(1985). This line presents HLA-A2. "G2.2" is a variant of the cell line MZ2-MEL. The variant has been transfected with a gene coding for HLA-A2. The abbreviation "G2.2.5" stands for a variant which does not express HLA-A2. All cells were incubated with monoclonal antibody MA2.1 prior to contact with the cytolytic T cell clone. This procedure stabilizes so-called "empty" MHC molecules, although the mechanism by which this occurs is not well understood and effector CTLs 210/5 and 210/9 were both used. The results are set forth in Table 5, which follows. They show that at a concentration of 10 μM, the nonamer of SEQ ID NO: 4 was twice as effective when used with CTL clone 210/5, and four times as effective with clone 210/9 whereas the nonamer of SEQ ID NO: 5 was ineffective at inducing lysis.

EXAMPLE 12

In further experiments, chromium release assays were carried out using the peptides of SEQ ID NOS: 4 and 5, as well as SEQ ID NO: 2. The target cells were allogeneic melanoma cells, i.e., MZ2-MEL, previously transfected with HLA-A2, and cell line T2, which presents HLA-A2, but has an antigen processing defect which results in an increased capacity to present exogenous peptides (Cerundolo et al., Nature 345: 449 (1990)). All cells were pretriated with monoclonal antibody MA2.1 for fifty minutes. The cells were incubated with the peptide of choice, for 30 minutes, at various concentrations. Then, one of CTL clones 210/9 and ISVB was added in an effector: target ratio of 60.

Chromium release was measured after four hours, in the manner described supra.

Figure 7C:
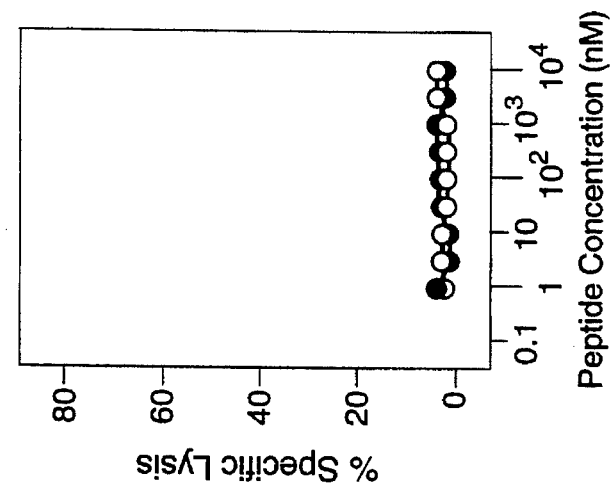
FIG. 7C sets forth results obtained using SEQ ID NO: 2.
Figure 7B:
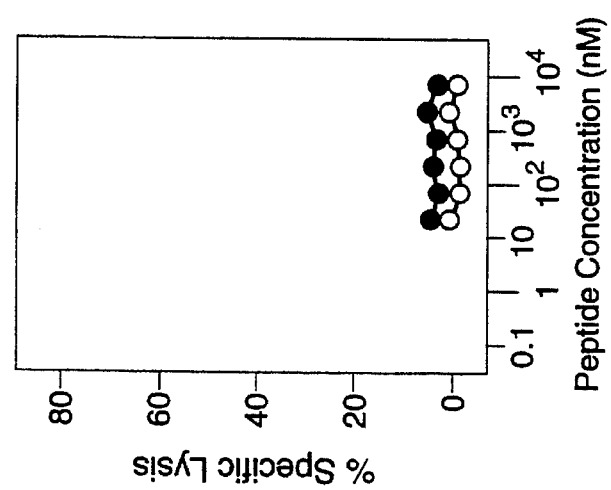
FIG. 7B shows results where the peptide of SEQ ID NO: 5 was used.
Figure 7A:
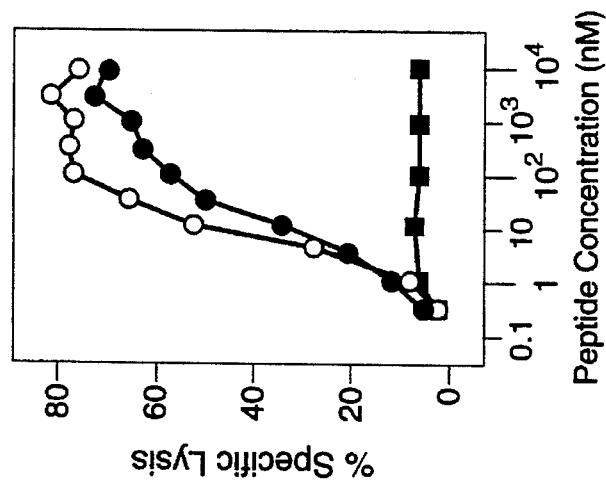
FIG. 7A presents experiments where the peptide of SEQ ID NO: 4 was used.
Figure 7F:
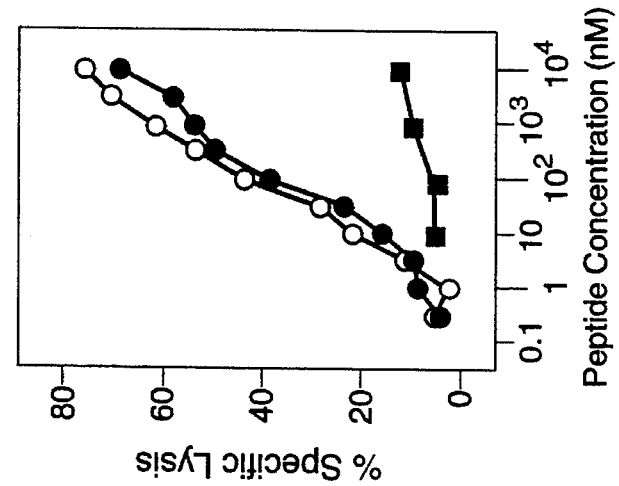
FIG. 7 shows, collectively, a series of chromium release assays using peptides described in this application on three different cell lines.
Figure 7E:
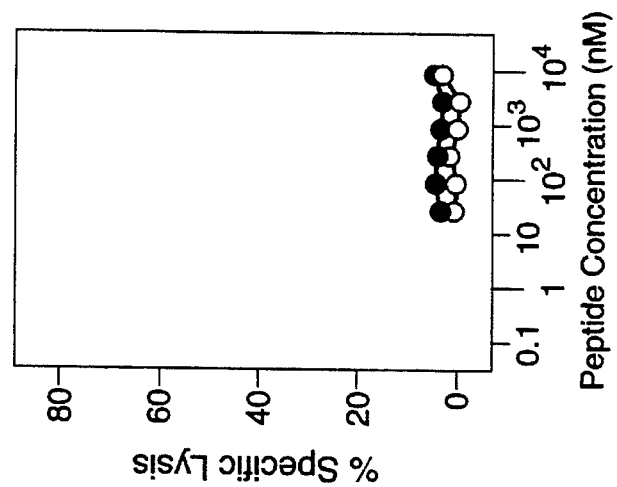
Figure 7D:
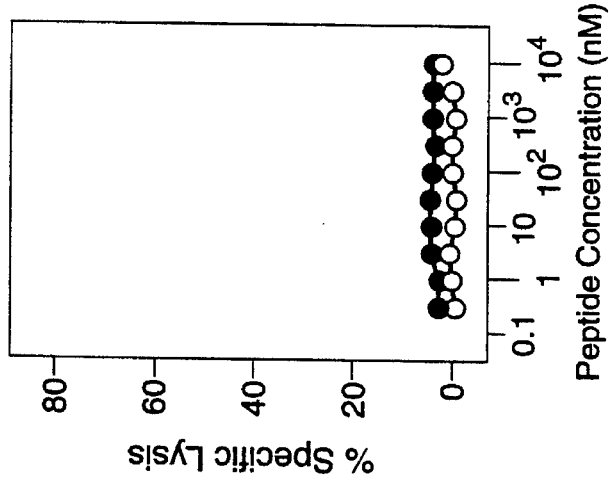

The results are presented in FIG. 7, i.e., FIGS. 7A–7C. The peptide of SEQ ID NO: 4 sensitized cells to CTL 210/9, while SEQ ID NO: 5 did not. SEQ ID NO: 2 sensitized cells to CTL IVSB, as already noted in previous examples.

| Test | complete | pept tyros | | | | | |
|---|---|---|---|---|---|---|---|
| 1 | 2 | | 3 | 4 | 5 | 6 | 7 |
| Effecteur | Peptide | | Dose | T2 +a-A2 | G2.2 +a-A2 | G2.2.5 + a-A2 | |
| 1 DAGI 210/5 | MLLAVLYCLL | | 10 μM | 50 | 32 | 2 | |
| 2 50:1 | (LAUS 17-5) | | 3 | 45 | 32 | 5 | |
| 3 | | | 1 | 39 | 26 | 3 | |
| 4 | | | 300 nM | 33 | 18 | 4 | |
| 5 | | | 100 | 24 | 8 | 5 | |
| 6 | | | 30 | 13 | 5 | 5 | |
| 7 | | | 10 | 6 | 5 | 5 | |
| 8 | | | 3 | 2 | 2 | 4 | |
| 9 | | | 1 | 2 | 1 | 3 | |
| 10 | | | 300 pg | 1 | 4 | 3 | |
| 11 | | | | | | | |
| 12 | MLLAVLYCL | | 10 μM | 98 | 65 | 7 | |
| 13 | (LAUS 19-5) | | 3 | 87 | 60 | 4 | |
| 14 | | | 1 | 95 | 66 | 5 | |
| 15 | | | 300 nM | 95 | 60 | 3 | |
| 16 | | | 100 | 91 | 56 | 3 | |
| 17 | | | 30 | 87 | 48 | 3 | |
| 18 | | | 10 | 82 | | 6 | |
| 19 | | | 3 | 78 | | 4 | |
| 20 | | | 1 | 76 | | 5 | |
| 21 | | | 300 pg | 78 | | 5 | |
| 22 | | | | | | | |
| 23 | LLAVLYCLL | | 10 μM | 0 | 1 | 3 | |
| 24 | (LAUS 19-10) | | 3 | 0 | 2 | 4 | |
| 25 | | | 1 | 3 | 3 | 3 | |
| 26 | 300 nM | | 0 | 2 | 4 | | |
| 27 | | | 100 | 1 | 2 | 4 | |
| 28 | | | 30 | 1 | 1 | 2 | |
| 29 | | | | | | | |
| 30 | YMNGTIMSQV | | 10 μM | 4 | 3 | 4 | |
| 31 | (MAINZ) | | 3 | 4 | 1 | 5 | |
| 32 | | | 1 | 2 | 2 | 4 | |
| 33 | | | 300 nM | 1 | 3 | 2 | |
| 34 | | | 100 | 0 | 1 | 6 | |
| 35 | | | 30 | 0 | 2 | 4 | |
| 36 | | | 10 | 0 | | 3 | |
| 37 | | | 3 | 3 | | 3 | |
| 38 | | | 1 | 2 | | 5 | |
| 39 | | | | | | | |
| 40 | 0 | | | 0 | 3 | 7 | |
| 41 | | | | | | | |
| 42 DAG 210/9 | MLLAVLYCLL | | 10 μM | 26 | 23 | 8 | |
| 43 60:1 | (LAUS 17-5) | | 3 | 20 | 23 | 6 | |
| 44 | | | 1 | 19 | 22 | 9 | |
| 45 | | | 300 nM | 13 | 16 | 7 | |
| 46 | | | 100 | 10 | 9 | 6 | |
| 47 | | | 30 | 5 | 6 | 7 | |
| 48 | | | 10 | 3 | 4 | 6 | |
| 49 | | | 3 | 5 | 9 | 5 | |
| 50 | | | 1 | 7 | 3 | 6 | |
| 51 | | | 300 pg | 1 | 4 | 8 | |
| 52 | | | 100 | 1 | 3 | 8 | |
| 53 | | | 30 | 1 | 4 | 7 | |
| 54 | | | | | | | |
| 55 | MLLAVLYCL | | 10 μM | 98 | 82 | 12 | |
| 56 | (LAUS 19-5) | | 3 | 92 | 75 | 10 | |
| 57 | | | 1 | 89 | 74 | 6 | |
| 58 | | | 300 nM | 95 | 67 | 6 | |
| 59 | | | 100 | 87 | 63 | 6 | |
| 60 | | | 30 | 93 | 53 | 5 | |
| 61 | | | 10 | 82 | 42 | 9 | |
| 62 | | | 3 | 87 | 34 | 8 | |
| 63 | | | 1 | 77 | 30 | 7 | |
| 64 | | | 300 pg | 70 | 25 | 7 | |
| 65 | | | 100 | 73 | 27 | 6 | |
| 66 | | | 30 | 41 | 22 | 6 | |
| 67 | | | | | | | |
| 68 | LLAVLYCLL | | 10 μM | 1 | 3 | 7 | |
| 69 | (LAUS 19-10) | | 3 | 1 | 3 | 8 | |

-continued

| | | | | | | Ven |
|---|---|---|---|---|---|---|
| | 8 Effecteur | 9 Peptide | 10 Dose | 11 T2 +a-A2 | 12 G2.2 +a-A2 | 13 G2.2.5 + a-A2 |
| 70 | | | 1 | 4 | 4 | 9 |
| 71 | | | 300 nM | 1 | 5 | 7 |

| | 8 Effecteur | 9 Peptide | 10 Dose | 11 T2 +a-A2 | 12 G2.2 +a-A2 | 13 G2.2.5 + a-A2 Ven |
|---|---|---|---|---|---|---|
| 1 | SK29 IVSB | MLLAVLYCLL | 10 μM | 3 | 3 | 7 |
| 2 | 60:1 | (LAUS 17-5) | 3 | 0 | 2 | 7 |
| 3 | | | 1 | 2 | 3 | 4 |
| 4 | | | 300 nM | 3 | 1 | 6 |
| 5 | | | 100 | 1 | 2 | 7 |
| 6 | | | 30 | 1 | 4 | 7 |
| 7 | | | 10 | 0 | 3 | 7 |
| 8 | | | 3 | 2 | 4 | 7 |
| 9 | | | 1 | 2 | 4 | 6 |
| 10 | | | 300 pg | 1 | 4 | 7 |
| 11 | | | | | | |
| 12 | | MLLAVLYCL | 10 μm | 2 | 3 | 6 |
| 13 | | (LAUS 19-5) | 3 | 1 | 4 | 6 |
| 14 | | | 1 | 0 | 4 | 6 |
| 15 | | | 300 nM | 1 | 3 | 7 |
| 16 | | | 100 | 1 | 4 | 6 |
| 17 | | | 30 | 0 | 4 | 6 |
| 18 | | | 10 | 0 | 4 | 6 |
| 19 | | | 3 | 1 | 4 | 6 |
| 20 | | | 1 | 1 | 3 | 8 |
| 21 | | | 300 pg | 0 | 3 | 6 |
| 22 | | | | | | |
| 23 | | LLAVLYCLL | 10 μM | 3 | 6 | 7 |
| 24 | | (LAUS 19-10) | 3 | 0 | 3 | 7 |
| 25 | | | 300 nM | 2 | 3 | 6 |
| 26 | | | 300 nM | 2 | 3 | 6 |
| 27 | | | 100 | 1 | 5 | 5 |
| 28 | | | 30 | 1 | 4 | 10 |
| 29 | | | | | | |
| 30 | | YMNGTMSQV | 10 μM | 78 | 69 | 8 |
| 31 | | (MAINZ) | 3 | 73 | 60 | 4 |
| 32 | | | 1 | 62 | 55 | 7 |
| 33 | | | 300 nM | 56 | 51 | 6 |
| 34 | | | 100 | 46 | 40 | 7 |
| 35 | | | 30 | 30 | 25 | 7 |
| 36 | | | 10 | 23 | 1 8 | 8 |
| 37 | | | 3 | 13 | 11 | 4 |
| 38 | | | 1 | 3 | 9 | 5 |
| 39 | | | 300 pg | 7 | 7 | 8 |
| 40 | | | 100 | 4 | 7 | 7 |
| 41 | | | 30 | 2 | 7 | 8 |
| 42 | | | | | | |
| 43 | | | 0 | 2 | 3 | 5 |
| 44 | | | | | | |
| 45 | | spl. rel | | 184 | 441 | 195 |
| 46 | | max. apt | | 1033 | 2522 | 1686 |
| 47 | | % | | 15 | 15 | 10 |

The foregoing experiments demonstrate that tyrosinase is processed as a tumor rejection antigen precursor, leading to formation of complexes of the resulting tumor rejection antigens with a molecule on at least some abnormal cells, for example, melanoma cells with HLA-A2 or HLA-B44 phenotype. The complex can be recognized by CTLs, and the presenting cell lysed. This observation has therapeutic and diagnostic ramifications which are features of the invention. With respect to therapies, the observation that CTLs which are specific for abnormal cells presenting the aforementioned complexes are produced, suggests various therapeutic approaches. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and are capable of provoking a specific CTL to proliferate. The target cell can be a transfectant, such as a COS cell of the type described supra. These transfectants present the desired complex on their surface and, when combined with a CTL of interest, stimulate its proliferation. So as to enable the artisan to produce these CTLs, vectors containing the genes of interest, i.e., pcDNA-1/Ampl (HLA-A2), and p123.B2 (human tyrosinase), have been deposited in accordance with the Budapest Treaty at the Institut Pasteur, under Accession Numbers I1275 and I1276, respectively. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257:238 (7-10-92); Lynch et al., Eur. J. Immunol. 21: 1403–1410 (1991); Kast et al., Cell 59:603–614 (11-17-89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present one or more of the HLA/tyrosinase derived peptide complexes. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for their HLA phenotype, using standard assays, and determines expression of tyrosinase via amplification using, e.g., PCR. The fact that a plurality of different HLA molecules present TRAs derived from tyrosinase increases the number of individuals who are suitable subjects for the therapies discussed herein.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining tyrosinase itself with an adjuvant to facilitate incorporation into HLA-A2 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

The invention also provides a method for identifying precursors to CTL targets. These precursors are referred to as tumor rejection antigens when the target cells are tumors, but it must be pointed out that when the cell characterized by abnormality is not a tumor, it would be somewhat misleading to refer to the molecule as a tumor rejection antigen. Essentially, the method involves identifying a cell which is the target of a cytolytic T cell of the type discussed supra. Once such a cell is identified, total RNA is converted to a cDNA library, which is then transfected into a cell sample capable of presenting an antigen which forms a complex with a relevant HLA molecule. The transfectants are contacted with the CTL discussed supra, and again, targeting by the CTL is observed (lysis and/or TNF production). These transfectants which are lysed are then treated to have the cDNA removed and sequenced, and in this manner a precursor for an abnormal condition, such as a tumor rejection antigen precursor, can be identified.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated peptide which consists of the amino acid sequence set forth in SEQ ID NO: 4.

* * * * *